(12) United States Patent
Lentz et al.

(10) Patent No.: US 9,629,653 B2
(45) Date of Patent: Apr. 25, 2017

(54) LOOPED WIRE CATHETER AND METHOD

(71) Applicant: Cook Medical Technologies LLC, Bloomington, IN (US)

(72) Inventors: David C. Lentz, Bloomington, IN (US); Thomas A. Kay, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 339 days.

(21) Appl. No.: 14/499,964

(22) Filed: Sep. 29, 2014

(65) Prior Publication Data

US 2015/0127032 A1    May 7, 2015

Related U.S. Application Data

(60) Provisional application No. 61/898,708, filed on Nov. 1, 2013.

(51) Int. Cl.
*A61B 17/3207* (2006.01)
*A61M 25/00* (2006.01)

(52) U.S. Cl.
CPC .. *A61B 17/320708* (2013.01); *A61B 17/3207* (2013.01); *A61B 2017/320733* (2013.01); *A61B 2017/320775* (2013.01); *A61M 25/005* (2013.01)

(58) Field of Classification Search
CPC ........ A61B 17/320708; A61B 17/3207; A61B 2017/32077; A61B 2017/320733; A61M 25/005

USPC ........ 606/159, 200, 113, 127, 108; 604/527, 604/540; 600/540, 585

See application file for complete search history.

(56) References Cited

U.S. PATENT DOCUMENTS

| 5,171,233 A * | 12/1992 | Amplatz | A61B 17/221 |
| | | | 604/540 |
| 6,620,179 B2 | 9/2003 | Boock et al. | |
| 8,070,693 B2 | 12/2011 | Ayala et al. | |
| 8,206,322 B2 * | 6/2012 | Hubregtse | A61B 17/00234 |
| | | | 600/585 |
| 9,320,535 B2 * | 4/2016 | Zaretzka | A61B 17/32002 |
| 9,408,625 B2 * | 8/2016 | Remmerswaal | A61B 17/32056 |
| 2006/0100544 A1 | 5/2006 | Ayala et al. | |

FOREIGN PATENT DOCUMENTS

EP    1620157    11/2011

* cited by examiner

*Primary Examiner* — Vy Bui
(74) *Attorney, Agent, or Firm* — Liell & McNeil

(57) ABSTRACT

A catheter includes a catheter body defining first and second lumens, and a wire having first and second segments each with a greater stiffness, and a middle segment with a lesser stiffness. The wire is in an elastically deformed access state where the middle segment extends from an opening to the first lumen to an opening to the second lumen and forms a smaller loop. The wire is adjustable via sliding the first and second segments in opposed directions to an elastically deformed treatment state where the first segment extends from the opening to the first lumen to the opening to the second lumen and forms a larger loop.

20 Claims, 3 Drawing Sheets

LOOPED WIRE CATHETER AND METHOD

TECHNICAL FIELD

The present disclosure relates generally to a catheter having a looped wire extending through first and second lumens, and more particularly to a looped wire catheter where the wire is elastically deformable between an access state forming a smaller loop, and a treatment state forming a larger loop.

BACKGROUND

A great many different designs for catheters, wires, tubes, sheath and other instruments are known from the field of interventional medicine. Typical catheter designs include an elongate tubular body, commonly formed of a polymer material, which is advanced into a patient's body for a variety of diagnostic and treatment purposes. In the case of percutaneously introduced catheters and the like, the elongate tubular body commonly has a longitudinally extending lumen by which the catheter can be tracked over a wire guide from an opening in the patient's skin into a body lumen of the patient such as a vein or artery. Catheters can be navigated through a patient's vasculature for a variety of different purposes, such as delivery of a therapeutic treatment agent, removal of undesired body tissue, and the treatment of injuries, damaged tissues and even congenital defects.

Clinicians can encounter a variety of challenges during catheter or other instrument navigation through the vasculature. Twists, turns and obstructions within a vein or artery can all present obstacles to navigating a treatment device to a desired location. With the ever decreasing size and sophistication of interventional devices to enable their navigation to smaller body lumens and sites more remote from a percutaneous entry point, the design, materials, and functional properties of interventional devices are of ever increasing importance.

Various materials which until relatively recently would have been considered exotic are now in routine use in the construction of catheters, wires and other interventional devices. So-called shape memory alloys are one example of materials having desirable and sometimes counterintuitive properties, and now commonly used. Such materials can enable devices such as wires, stents, snares and other tools to be adjusted from a very small, low profile state for introduction into a patient's body and navigation to a site of interest, to a deployed state for treating the patient. One known interventional device configured for navigation through body lumens is disclosed in commonly owned U.S. Pat. No. 8,070,693 to Ayala et al.

SUMMARY OF THE DISCLOSURE

In one aspect, a catheter includes an elongate catheter body defining a first lumen and a second lumen each longitudinally extending between a proximal end and a distal end of the elongate catheter body and including a first lumen opening and a second lumen opening, respectively, in the distal end. The catheter further includes a wire having a first segment and a second segment each with a greater stiffness and slidable in opposed directions through the first lumen and the second lumen, respectively, and a middle segment having a lesser stiffness. The wire is in an elastically deformed access state where the middle segment extends from the first lumen opening to the second lumen opening and forms a smaller loop projecting from the distal end. The wire is adjustable via the sliding to an elastically deformed treatment state where the first segment extends from the first lumen opening to the second lumen opening and forms a larger loop projecting from the distal end.

In another aspect, a method of deploying a catheter for treatment of a patient includes sliding first and second greater stiffness segments of a wire in opposed directions through first and second longitudinally extending lumens in a catheter, and positioning the first segment via the sliding in place of a lesser stiffness middle segment of the wire extending between the first and second lumens. The method still further includes adjusting the wire via the positioning from an elastically deformed access state where the middle segment forms a smaller loop projecting from a distal end of the catheter to an elastically deformed treatment state where the first segment forms a larger loop projecting from the distal end.

DETAILED DESCRIPTION

Figure 1:
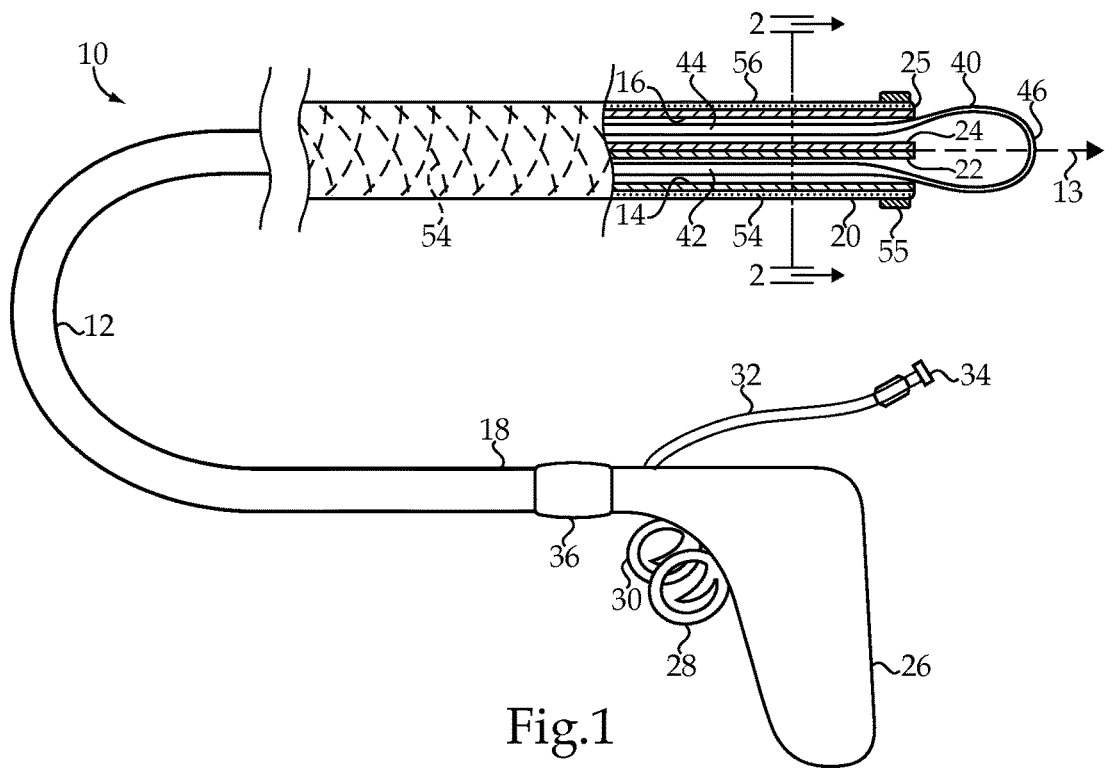
FIG. 1 is a partially sectioned side diagrammatic view of a catheter, according to one embodiment.

Referring to FIG. 1, there is shown a catheter 10 according to one embodiment, and including an elongate catheter body 12 defining a longitudinal axis 13. Body 12 further defines a first lumen 14 and a second lumen 16 each longitudinally extending between a proximal end 18 and a distal end 20 of body 12. First lumen 14 includes a first lumen opening 22, and second lumen 16 includes a second lumen opening 24, each formed in distal end 20. More particularly, lumen openings 22 and 24 may be formed in a distal tip 25 of body 12. Catheter 10 further includes a wire 40 having a first segment 42 and a second segment 44 each with a greater stiffness and being slidable in opposed directions through first lumen 14 and second lumen 16, respectively. Wire 40 further includes a middle segment 46 having a lesser stiffness. Wire 40 is in an elastically deformed access state, for accessing a body lumen in a patient, where middle segment 46 extends from first lumen opening 22 to second lumen opening 24 and forms a smaller loop projecting from distal end 20. As will be further apparent from the following description and accompanying drawings, wire 40 is adjustable via the sliding of first and second segments 42 and 44 in the opposed directions to an elastically deformed treatment state where first segment 42 extends from first lumen opening 22 to second lumen opening 24 and forms a larger loop projecting from distal end 20.

Catheter 10 may further include a handle mechanism 26 coupled to proximal end 18, handle mechanism 26 including a first actuator 28 and a second actuator 30. Actuators 28 and 30 may be coupled directly to wire 40, and in particular wire segments 42 and 44, respectively, to enable a clinician to adjust wire 40 via the sliding of wire segments 42 and 44. Those skilled in the art will appreciate that actuators 28 and 30 may be used to push one of wire segments 42 and 44 while simultaneously pulling the other of wire segments 42 and 44 to enable the sliding in opposed directions. A leader tube 32 is coupled to handle mechanism 26 and includes a fitting 34. Leader tube 32 may define part of a longitudinally extending working lumen in body 12, which also opens at distal tip 25 but is hidden from view in the FIG. 1 illustration. The subject working lumen may be used for tracking catheter 10 over a wire guide extending from a location outside of a patient into a body lumen in the patient, and for other purposes as further discussed herein.

Figure 2:
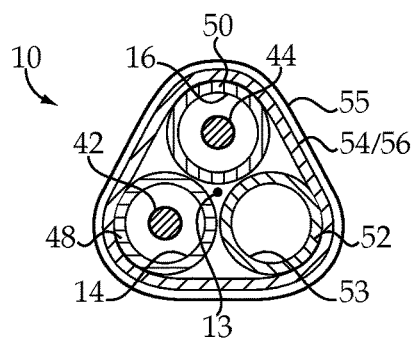
FIG. 2 is a sectioned view taken along line 2-2 of FIG. 1.

Referring also now to FIG. 2, there is shown a sectioned view taken along line 2-2 of FIG. 1. A first tube section 48 of catheter body 12 defines lumen 14, and a parallel second tube section 50 defines lumen 16. A third tube section 52 is also visible in the sectioned view, and defines a working lumen 53 as described above. In the illustrated embodiment, catheter 10 is a three lumen catheter, but in other versions four or even more lumens might be used, or only the two lumens to accommodate wire 40. In one practical implementation strategy, catheter 10 further includes a reinforcement 54 within distal end 20. Reinforcement 54 may extend circumferentially around each of first lumen 14 and second lumen 16, and in the illustrated embodiment includes a metallic braid 54 that extends all the way around each of the three tube sections 48, 50 and 52. In alternative embodiments, each of the tubes of catheter body 12 might be individually wrapped with a reinforcement braid or the like. While it is contemplated that catheter body 12 might be made from a single extrusion defining the two or more lumens, in other embodiments individual extruded tube elements might be attached to one another. A coating or casing material 56 may be used to secure reinforcement 54 to catheter body 12, and might include a polymeric material such as a polyamide based material melt flowed over the extrusion or individual elements forming tube sections 48, 50 and 52. Typically, a polyamide based material such as Nylon, PEBA or polyurethane will be used for the extrusion(s). Individual liners forming a core within a base tube or the like might be polyimide or PTFE based. If deemed necessary, an additional split prevention reinforcement 55 may be mounted at the distal end 20 of elongate catheter body 12. The split prevention reinforcement 55 may take the form of a band of material, such as a swaged or machined metal band that is mounted at the distal end 20 of catheter body 12 so that neither the distal tip 25 of catheter body 12 nor the reinforcement 54 will split or fray under the interaction with wire 40.

Figure 3:
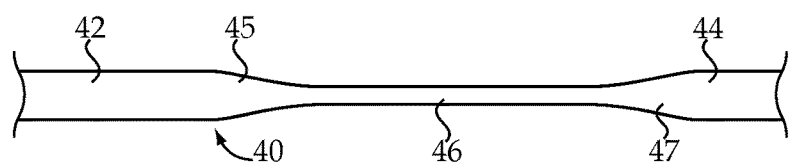
FIG. 3 is a diagrammatic view of a portion of a wire in the catheter of FIG. 1.

Referring now also to FIG. 3, there is shown a portion of wire 40 as it might appear in a rest state, in other words not elastically deformed. There can be seen middle segment 46 joining first segment 42 and second segment 44. A first middle segment 46 may include a first taper 45 transitioning with first segment 42, and a second taper 47 transitioning with second segment 44. Wire 40 may include a one-piece wire formed of a shape memory material having a uniform elastic limit throughout. Those skilled in the art will be familiar with the term elastic limit, referring to a condition of internal stress within a material beyond which plastic deformation results. The shape memory material of which wire 40 is formed, such as nitinol or another suitable material, therefore may have consistent material properties everywhere within wire 40. Different geometry of middle segment 46 versus first and second segments 42 and 44, however, imparts the differing stiffnesses. As used herein, the term stiffness is to be understood in reference to a bending moment of inertia of the subject wire segment. Accordingly, relatively lesser stiffness middle segment 46 may have a lesser bending moment of inertia, whereas first and second segments 42 and 44 may have relatively greater bending moments of inertia, the significance of which will be apparent from the following description.

Also in a practical implementation strategy, wire 40 may have a circular cross-sectional shape, with first and second segments 42 and 44 being longer segments having a circular cross-sectional shape with a greater area, and middle segment 46 being a shorter segment having a concentric circular cross-sectional shape with a lesser area. Delineation between first segment 42 and middle segment 46, and between middle segment 46 and second segment 44, is not arbitrary. A transition between what is fairly considered first segment 42 or second segment 44 and middle segment 46 can be understood to reside where a change in stiffness beyond manufacturing tolerances occurs. Accordingly, in FIG. 3 where an outer diameter dimension or thickness of wire 40 begins to change transitioning from first segment 42 to taper 45, a difference in stiffness will typically be detectable manually or at least with routinely available instruments, and analogously with respect to taper 47 and second segment 44. Thus, in the illustrated embodiment of FIG. 3, traveling to the right middle segment 46 begins at just the point where taper 45 begins, and ends at just the point where taper 47 ends and transitions to second segment 44. It is contemplated that reducing material volume of wire 40, such as by grinding, to form reduced diameter middle segment 46 provides a practical implementation strategy. In alternative embodiments, however, different material compositions or treatment strategies such as heat treatment might potentially be used to obtain a wire having the desired properties of varying stiffness.

It will be recalled that wire 40 is shown in FIG. 1 in an elastically deformed access state, and is adjustable via the sliding of segments 42 and 44 to an elastically deformed treatment state. In the access state, middle segment 46 is that segment of wire 40 which extends out of catheter body 12 and forms the smaller loop, whereas in the treatment state it is one of wire segments 42 and 44 which is positioned in place of wire segment 46 and extends out of catheter body 12 to form the larger loop. It has been discovered that certain wire material compositions and configurations may prevent such wires from being elastically deformed into a tight enough loop for access through a relatively small access sheath into body lumens in a patient. By providing wire 40 with a configuration where part of the wire has a lesser stiffness, that lesser stiffness part of the wire may form the loop for accessing a body lumen in a patient, but be swapped for the relatively stiffer section of the wire for treatment.

One advantageous application of catheter 10 is to cutting material within a body lumen in a patient. It has been discovered that a wire of about 0.012 inches outer diameter dimension or greater provides sufficient column support to enable cutting of material such as thrombus material when formed into a loop. A loop formed from a wire of such a thickness, however, may have problems with respect to sheath compatibility. For instance, a looped 0.014 inch wire inserted through a 6 French sheath having a 0.075 inch inner diameter dimension will tend to plastically deform, negatively impacting that wire's cutting ability. Analogously, a looped 0.010 inch wire inserted through a 5 French sheath with a 0.063 inch inner diameter dimension may exhibit similar problems as to plastic deformation. Plastic deformation, or "set," in the wire can prevent the device from effectively performing a desired cutting function. The relatively large loop required with such size wires to avoid a set might also damage a hemostasis mechanism, or shaft of an access sheath as noted above. The present disclosure contemplates retaining advantageous cutting features of a looped wire without creating such sheath compatibility issues, via the reduced thickness middle wire segment 46. A 0.014 inch wire can be ground down to about 0.009 inches over a span from about 1 to about 2 inches to create a lesser stiffness middle segment. The overall length of such a wire might be 3-9 feet from tip to tip. It may be noted that this reduction in diameter is from about 30% to about 35%, more particularly about 33%, of the wire diameter. These parameters can be expected to scale up or down. Accordingly, a wire about 0.010 thousandths inches in diameter might be reduced in diameter from about 30% to about 35%, to enable its use in a 5 French access sheath as noted above. Those skilled in the art will readily understand how these relative dimensions translate to differences in cross-sectional area, thus differences in bending moment of inertia, for a lesser stiffness middle wire segment versus greater stiffness adjoining first and second wire segments. As used herein, the term "about" should be understood in the context of conventional rounding to a consistent number of significant digits. Accordingly, "about" 10 means from 9.5 to 10.4, and so on.

Figure 4:
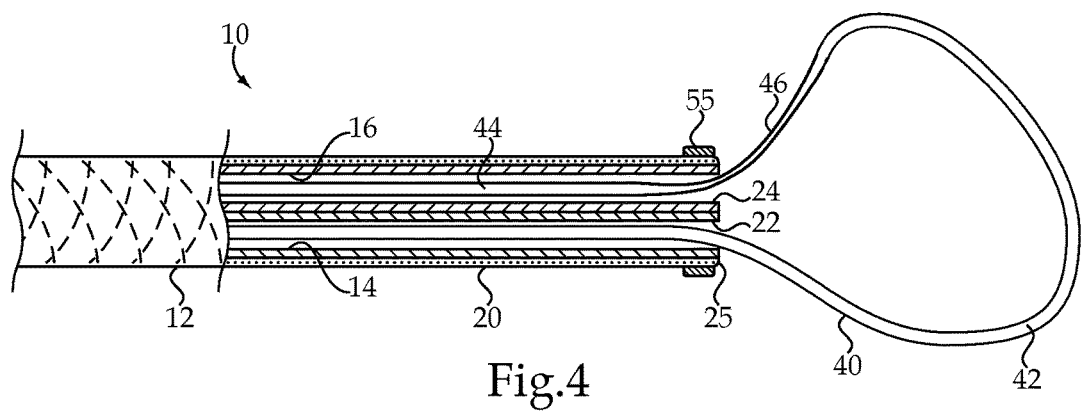
FIG. 4 is a partially sectioned side diagrammatic view of a portion of the catheter of FIG. 1, where the wire is shown adjusted part way between an access state and a treatment state.
Figure 5:
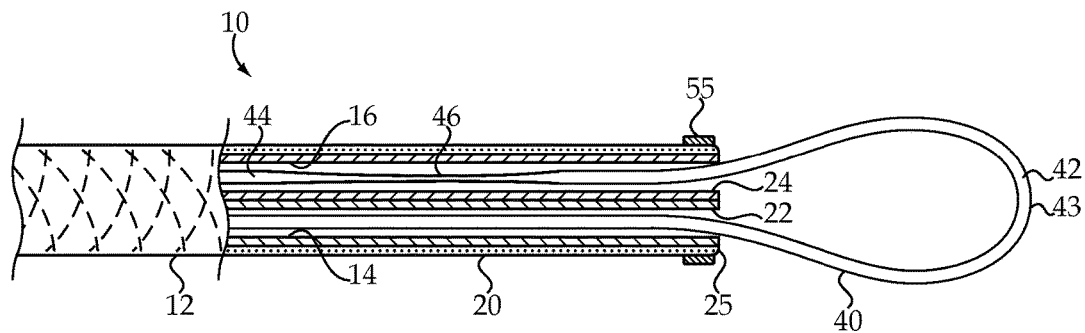
FIG. 5 is a view similar to FIG. 4, where the wire is in the treatment state.

Referring now to FIG. 4, there is shown catheter 10 as it might appear where wire segment 42 has been advanced out of lumen 14, and middle wire segment 46 has begun to be fed into lumen 16. At the state shown in FIG. 4, first segment 42 extends out of lumen opening 22 but middle segment 46 extends into lumen opening 24. It may be noted that lesser stiffness middle segment 46 bulges radially outwardly, with respect to the longitudinal axis of catheter 10, as compared with segment 42 given the difference in stiffnesses. Referring also now to FIG. 5, there is shown catheter 10 as it might appear where wire 40 has been adjusted to the treatment state where wire segment 42 extends out of lumen opening 22 and into lumen opening 24 to form the larger loop. In FIG. 5, a leading edge of wire 42 is shown via numeral 43. It may be noted that the larger loop formed by segment 42 is about twice an outer diameter dimension of catheter body 12, and may be greater in some applications.

Figure 6:
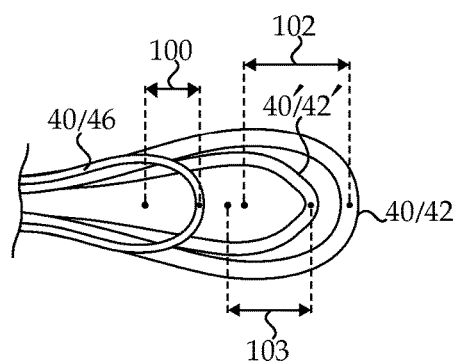
FIG. 6 is a concept illustration showing actual and theoretical configurations of the wire.

Referring now to FIG. 6, there is shown a concept diagram where the smaller loop formed by segment 46 is shown overlaying the larger loop formed by segment 42. Segment 46 defines a smaller loop radius 100, whereas the larger loop formed by segment 42 defines a larger loop radius 102. It will be recalled that wire 40 is elastically deformed in both the access state and the treatment state. Accordingly, the looping portions of wire 40 shown in FIG. 6 as segment 46 and segment 42 could be expected to return to a linear state when no external biasing force is applied. For that matter, an entirety of wire 40 may be substantially straight-line linear at rest. Also shown in FIG. 6 is wire 40' where a segment 42' has begun to plastically deform, in other words where wire 40' has been tightened into a loop small enough that elasticity of the material is overcome, and plastic deformation begins. Approximately at the state where plastic deformation of wire 40' begins, wire 40' defines a bend radius of plastic deformation 103. It may be noted that a size of radius 103 is less than radius 102, but that a size of radius 100 is less than radius 103. Another way to understand the principles represented in FIG. 6 is that middle segment 46 is elastically deformed to a loop size less than a loop size to which segment 42 or segment 44 can be deformed without plastic deformation of the material, in other words the wire taking a set.

INDUSTRIAL APPLICABILITY

Figure 7:
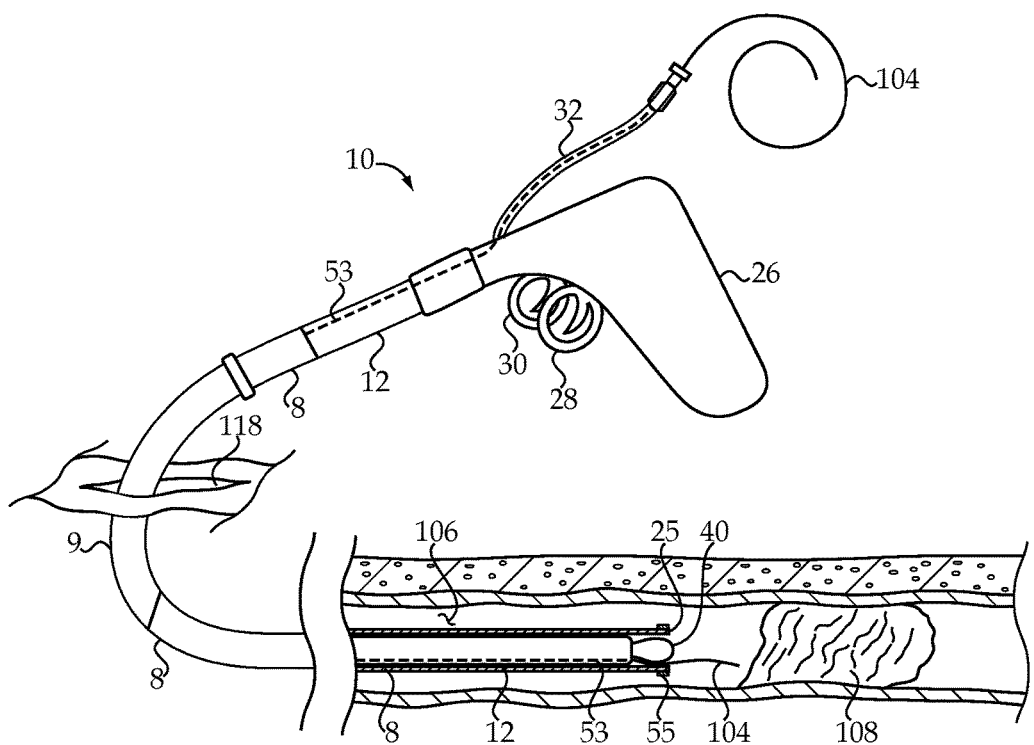
FIG. 7 is a side diagrammatic view of the catheter at one stage of a treatment procedure, according to one embodiment.

Referring to the drawings generally but in particular now to FIG. 7, there is shown catheter 10 as it might appear being advanced over a wire guide 104 into a body lumen 106 such as a vein or artery in a patient. It can be seen that wire guide 104 extends through leader 32, and thenceforth through working lumen 53 and out distal tip 25 of catheter 10. Catheter 10 passes through an introducer 9 extending through an opening 118 in the patient's skin, and is positioned within an access sheath 8. It will be recalled that wire 40 is configurable in an access state where a smaller loop projects from distal tip 24. The smaller loop is shown in FIG. 7 and positioned within access sheath 8. Catheter 10 within sheath 8 is positioned in proximity to a thrombus 108 in body lumen 106. From the state depicted in FIG. 7, sheath 8 may be withdrawn, and wire guide 104 may be removed entirely from catheter 10.

Figure 8:
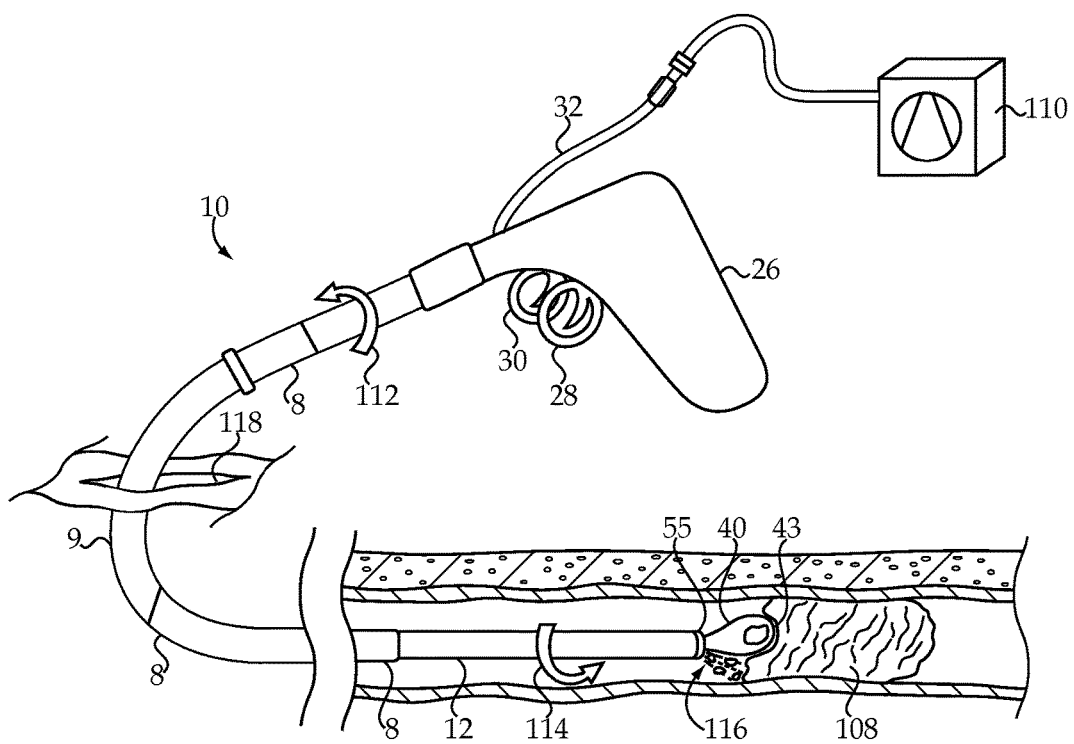
FIG. 8 is a side diagrammatic view of the catheter at another stage of the treatment procedure.

Referring now to FIG. 8, there is shown catheter 10 as it might appear where sheath 8 has been withdrawn, and actuators 28 and 30 have been used to slide the first and second segments 42 and 44 of wire 40 in opposed directions through first and second lumens 14 and 16, positioning first segment 42 in place of middle segment 46, and thereby adjusting wire 40 to its treatment state where first segment 42 forms the larger loop projecting from distal end 25. The adjusting of wire 40 in this general manner may be understood as relieving a load, in particular from an internal shape memory bias of wire 40, on middle segment 46. Adjusting wire 40 may also be understood as applying a load, via the shape memory bias, to first segment 42. Thus, first and second segments 42 and 44 will tend to be at rest within lumens 14 and 16 in the access state of wire 40. When wire 40 is adjusted to the treatment state, segment 42 may be loaded via the shape memory bias, and segment 44 may be un-loaded to rest.

It will also be understood that a tendency for at least the larger loop, and in some instances the smaller loop, to flair outwardly of distal tip 25 can result in impinging of the loaded middle segment 46 and the loaded first segment 42 upon inner walls of catheter 10 defining first and second lumens 14 and 16. Such impingement may occur more or less continuously due to the tendency for wire 40 to elastically rebound toward a linear configuration, but may be most acute during adjusting wire 40 from the access state to the treatment state, where segments 42 and 46 are sliding against material of catheter 10. Reinforcement 54 can have the desirable effect of limiting penetration of the impinging middle and first segments 46 and 42 through catheter 10, and thus limiting splitting at distal tip 25. As such, in a practical implementation strategy reinforcement 54 may extend all the way from proximal end 18 to distal tip 25. Alternatively, or in addition, a split prevention reinforcement 55 may be included in order to inhibit wire 40 from fraying reinforcement 54 and/or splitting the distal end 20 of catheter body 12. Those skilled in the art will appreciate that the split prevention reinforcement 55 may preferably come in the form of a band of a suitable material attached to distal end 20 of catheter body 12 and/or reinforcement 54.

With the larger loop formed in the treatment state, wire 40 may be used to cut material of thrombus 108 via leading edge 43 and other parts of segment 42, and can be rotated within body lumen 106 via transmitting a torque applied to proximal end 18 to distal end 20. Torque arrows 112 and 114 illustrate such operation in FIG. 8. It will be recalled that reinforcement 54 may extend longitudinally all or most of the way through catheter body 12. In addition to limiting penetration of wire 40 into and through catheter 12 at distal tip 25, reinforcement 54, noted above as potentially a metallic braid, can enhance the capability of transmitting the torque for cutting.

It will further be recalled that catheter 10 is guided prior to deployment through body lumen 106 via advancing over wire guide 104, extending through working lumen 53 generally parallel first and second lumens 14 and 16. With wire guide 104 withdrawn or even potentially with wire guide 104 still in place, working lumen 53 becomes available for the injection of a fluid into body lumen 106, as well as withdrawal of fluid via suction. In FIG. 8, a vacuum pump 110 or the like is shown connected via leader 32 to catheter 10, and can be used to create a suction stream 116 drawing fluid as well as fragments of thrombus cut via wire 40 through catheter 10 and out of the patient.

In addition to removing cut material from a body lumen via suction, the working lumen could also be used to inject a thrombolytic agent or the like to assist in breaking up and/or dissolving material of the thrombus. When the material of thrombus 108 has been sufficiently or entirely cleared from body lumen 106 to restore a flow of blood therethrough, wire 40 may be returned from the elastically deformed treatment state to the elastically deformed access state, by sliding segments 42 and 44 in directions opposite to those used in deploying catheter 10. As a result, wire 40 may be adjusted such that segment 46 once again extends between lumens 14 and 16 and forms a smaller loop. Sheath 8 can then be advanced back over catheter 10, past distal tip 25, and catheter 10 removed from the patient.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. For instance, while the present description is focused on use of catheter 10 in a thrombectomy procedure, catheter 10 might instead be used in other applications in the body. It is also contemplated that in addition to cutting material such as thrombus material within a body lumen, wire 40 may be used in catheter 10 to assist in introducing and mechanically mixing therapeutic agents such as thrombolytic agents or anticoagulants into clots, potentially delivered via working lumen 53. Other aspects, features and advantages will be apparent upon an examination of the attached drawings and appended claims.

What is claimed is:

1. A catheter comprising:
    an elongate catheter body defining a first lumen and a second lumen each longitudinally extending between a proximal end and a distal end of the elongate catheter body and including a first lumen opening and a second lumen opening, respectively, in the distal end;
    a wire including a first segment and a second segment each having a greater stiffness and slidable in opposed directions through the first lumen and the second lumen, respectively, and a middle segment having a lesser stiffness; and
    the wire being in an elastically deformed access state where the middle segment extends from the first lumen opening to the second lumen opening and forms a smaller loop projecting from the distal end, and being adjustable via a sliding to an elastically deformed treatment state where the first segment extends from the first lumen opening to the second lumen opening and forms a larger loop projecting from the distal end.

2. The catheter of claim 1 wherein the wire includes a one-piece wire formed of a shape memory material having a uniform elastic limit throughout.

3. The catheter of claim 2 wherein the first segment and the second segment each define a bend radius of plastic deformation, and the smaller loop defines a loop radius less than the bend radius.

4. The catheter of claim 3 wherein the elongate catheter body defines an outer diameter body dimension, and the smaller loop defines an outer diameter loop dimension equal to about twice the outer diameter body dimension, or less.

5. The catheter of claim 1 wherein each of the first and second segments is longer and has a greater cross-sectional area, and the middle segment is shorter and has a reduced cross-sectional area.

6. The catheter of claim 3 wherein each of the first and second segments includes a circular cross-sectional shape, and the middle segment has a concentric circular cross-sectional shape.

7. The catheter of claim 1 further comprising a reinforcement within the distal end.

8. The catheter of claim 7 wherein the distal end includes a distal tip, and the reinforcement extends circumferentially around each of the first and second lumens, and longitudinally through the elongate catheter body from the proximal end to the distal tip.

9. The catheter of claim 7 wherein the reinforcement includes a braid.

10. The catheter of claim 7 wherein the elongate catheter body defines a third lumen extending in parallel with each of the first and second lumens and opening at the distal end.

11. The catheter of claim 1 further comprising a split prevention reinforcement mounted at the distal end of the elongate catheter body.

12. The catheter of claim 11 wherein the split prevention reinforcement includes a band mounted around the distal end of elongate catheter body.

13. A method of operating a catheter that includes an elongate catheter body defining a first lumen and a second lumen each longitudinally extending between a proximal end and a distal end of the elongate catheter body and including a first lumen opening and a second lumen opening, respectively, in the distal end; a wire including a first segment and a second segment each having a greater stiffness and slidable in opposed directions through the first lumen and the second lumen, respectively, and a middle segment having a lesser stiffness; and the wire being in an elastically deformed access state where the middle segment extends from the first lumen opening to the second lumen opening and forms a smaller loop projecting from the distal end, and being adjustable via a sliding to an elastically deformed treatment state where the first segment extends from the first lumen opening to the second lumen opening and forms a larger loop projecting from the distal end, and the method comprising the steps of:
    sliding the first and second greater stiffness segments of the wire in opposed directions through the first and second longitudinally extending lumens in the catheter;
    positioning the first segment via the sliding in place of the lesser stiffness middle segment of the wire extending between the first and second lumens; and adjusting the wire via a positioning from the elastically deformed access state where the middle segment forms the smaller loop projecting from the distal end of the catheter to the elastically deformed treatment state where the first segment forms a larger loop projecting from the distal end.

14. The method of claim 13 further comprising a step of relieving a load on the middle segment and applying a load to the first segment, via the adjusting of the wire.

15. The method of claim 14 further comprising a step of impinging the loaded middle segment and loaded first segment upon inner walls of the catheter defining the first and second lumens during the adjusting of the wire.

16. The method of claim 15 further comprising a step of limiting penetration of the impinging middle and first segments through the catheter via a reinforcement in the distal end.

17. The method of claim 13 further comprising a step of guiding the catheter prior to deployment through a body lumen in a patient via a wire guide extending through a third, working lumen extending in parallel with the first and second lumens.

18. The method of claim 17 further comprising a step of cutting material within the body lumen via a leading edge of the larger loop so as to restore a flow of blood through the body lumen.

19. The method of claim 18 further comprising a step of transmitting a torque applied to a proximal end of the catheter to the distal end via a braid within the catheter so as to cut the material via rotation of the larger loop.

20. The method of claim 18 further comprising a step of removing cut material from the body lumen via suction applied to the working lumen.

* * * * *